United States Patent [19]

Yokoi et al.

[11] Patent Number: 5,348,576
[45] Date of Patent: Sep. 20, 1994

[54] ANTIFOULING COMPOSITION

[75] Inventors: Junji Yokoi; Akio Harada, both of Nara, Japan

[73] Assignee: Nippon Paint Co., Ltd., Osaka, Japan

[21] Appl. No.: 849,607

[22] Filed: Mar. 11, 1992

[30] Foreign Application Priority Data

Mar. 12, 1991 [JP] Japan .................. 3-127025

[51] Int. Cl.$^5$ .............................................. C09D 5/14
[52] U.S. Cl. ........................ 106/15.05; 106/18.29; 106/18.32; 106/18.33; 106/18.34; 106/18.35; 424/78.09; 514/717; 514/718; 514/731; 514/738; 523/122
[58] Field of Search ............ 106/15.05, 18.29, 18.32, 106/18.33, 18.34, 18.35; 71/67; 424/78.09; 514/717, 718, 731, 738; 523/122

[56] References Cited

U.S. PATENT DOCUMENTS

| | | | |
|---|---|---|---|
| 5,116,611 | 5/1992 | Masuoka et al. | 106/15.05 |
| 5,154,747 | 10/1992 | Yokoi et al. | 106/15.05 |

FOREIGN PATENT DOCUMENTS

| | | |
|---|---|---|
| 53-121928 | 10/1978 | Japan . |
| 59-170162 | 9/1984 | Japan . |
| 60-028904 | 2/1985 | Japan . |
| 64-014282 | 1/1989 | Japan . |
| 1178458 | 7/1989 | Japan . |
| 90333325 | 11/1990 | Japan . |

*Primary Examiner*—Anthony Green
*Attorney, Agent, or Firm*—Wenderoth, Lind & Ponack

[57] ABSTRACT

An antifouling composition for coating fishnets consisting essentially of (A) at least one phenol compound represented by the formula:

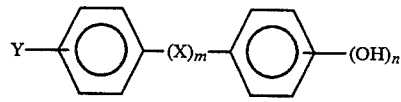

or the formula:

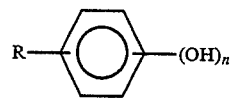

(in which Y is hydrogen atom or hydroxyl group;

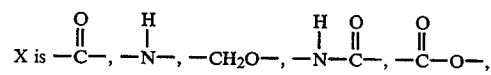

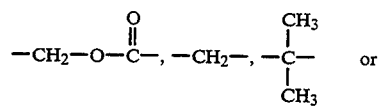

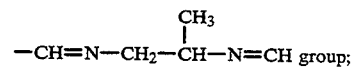

m is 0 or 1; n is an integer of 1-5; R is a linear or branched alkyl having 4 to 21 carbon atoms), (B) at least one water-repellent organic compound selected from silicone oil, petroleum wax and liquid paraffins, and (C) at least one antifouling agent selected from fluorodichloromethyl thiophthalimide, dimethylphenyl fluorodichloromethyl thiosulfamide and dichlorophenyl dimethyl urea, the amount of said (C) being 0.5-20 wt % of the total of (A)+(B)+(C).

The present antifouling composition is specifically effective for the prevention of attachment, and proliferation of noxious aquatic organisms including both of an animal and botanical nature.

1 Claim, No Drawings

ANTIFOULING COMPOSITION

BACKGROUND OF THE INVENTION

Field of the Invention

The present invention relates to an antifouling composition to be applied to fishnets and the like which prevents attachment and proliferation of noxious aquatic organisms thereon.

Description of the Related Art

Various noxious aquatic organisms such as barnacles, hardshell mussels, sea lettuce and the like are usually deposited on and attached to fishnets, such as fixed-nets, fish preserve nets, basket-like fishnets and the like. Being placed in sea-water, the attachment of these organisms to ropes, buoys and the cause clogging of the nets, a weight increase in the nets and the like.

In the worst case, there results a marked decrease in catch in the fixed-net, and a growth-failure and death of culture fishes or shell-fishes in the fish preserve or the like due to oxygen shortage.

As for previously known measures for preventing such problems, tarcoating and chemical coating have long been practiced. For example, fishnets or the like have heretofore been coated with an antifouling paint containing copper powder, a copper compound or organotin compound as a toxic material. Most widely used antifouling paints are based on organotin compounds such as tributyl tin compound, triphenyl tin compound and the like, and high-molecular weight compounds containing such organotin moiety.

However, such antifouling paints containing heavy metal compounds are rather undesirable from the standpoint of environmental pollution and hygiene because the catch is used for food.

The present inventors have previously proposed an antifouling paint for noxious aquatic organisms consisting essentially of an alkyl phenol derivative and a water repellant compound in Japanese Patent Application No, 59344/90, and an antifouling paint consisting essentially of a substituted aromatic phenol compound and a water repellent compound in Japanese Patent Application No. 333325/90.

These antifouling paints are characterized in that dissolution of the active ingredient into sea-water is extremely low and the adhesion of noxious aquatic organisms to fishnets and the like is effectively controlled by the surface activity of the coated surface, resulting from the formation of both hydrophobic and hydrophilic groups thereupon.

Such function is very desirable in that there is the least dissolution of toxic material in sea-water and these paints are indeed effective for the control of noxious aquatic animal organisms. However, these paints are not effective in controlling botanical stain, so there is room for further studies form the standpoint of effective control of staining plants.

It is, therefore, an object of the invention to provide an antifouling composition which is free from the heretofore known various problems in antifouling effectiveness, safety environmental, hygienic and food sanitation aspects. That is, said composition should preferably give the least dissolution of toxic material in seawater, cause no residual problem or adverse effects on the life of other sea-living organisms, and be able to markedly prevent the attachment of proliferation of noxious aquatic organisms including both of an animal and botanical nature on fishnets.

According to the present invention, the abovementioned object the present invention can be attained by the present antifouling composition which essentially consists of (A) at least one phenol compound represented by the formula:

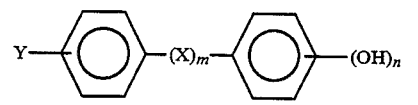

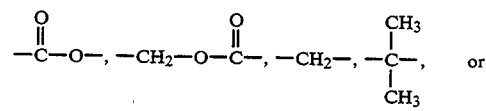

group; m is 0 or 1; Y is hydrogen atom or hydroxyl group; and n is an integer of 1 to 5) or the formula:

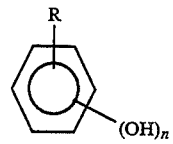

in which R is a linear or branched alkyl having 4 to 21 carbon atoms; and n is an integer of 1-5.

(B) at least one water-repellent organic compound selected from the group consisting of silicone oil, petroleum wax, and liquid paraffin, and (C) at least one anti fouling agent selected from the group consisting of fluorodichloromethyl thiophthalimide, dimethyl phenyl fluorodichloromethyl thiosulfamide and dichlorophenyl dimethyl urea, the amount of said antifouling agent being 0.5-20% by weight of the total off said (A)+(B)+(C).

Among the antifouling agents stated in (C), fluorodichloromethyl thiophthalimide has already been proposed as a toxicant in an antifouling paint for fishnet, as disclosed in Japanese Patent Publication (unexamined) 121928/78 and 28904/85. Dimethyl phenyl fluorodichloromethyl thiosulfamide has also been proposed for the similar purpose in Japanese Patent Publication (unexamined) 8904/85. Dichlorophenyl dimethyl urea is a well-known agricultural chemical and in an antifouling paint area, it has also been proposed as a toxicant in Japanese Patent Publication (unexamined) 170162/84 and 14282/89.

Thus, the abovenamed compounds each has already been proposed as an active ingredient of an anti fouling paint. However, they are, when dissolved in sea-water, immediately hydrolyzed and decomposed to non-toxic materials. Therefore, the desired antifuling effect can never be maintained for a longer time and hence, a considerable quantity of such toxicant must used in an anti fouling paint.

In fact, the mere combination of the phenolic compound, the water-repellent organic compound and the abovementioned antifouling agent was not effective for the control of noxious aquatic organisms in a longer duration of time intended, and in certain cases, there was instead a decrease in the antifouling effect itself.

Very surprisingly, the inventors have found that in a particular quantity of said antifouling agent (C), the very desired antifouling effect on both animal and botanical, noxious aquatic organisms can be obtained with the combination of phenolic compound (A), water-repellent organic compound (B) and the said antifouling agent (C).

In the present invention, the said antifouling agent (C) not intended to be the main toxicant of the antifouling paint, but is used only as a supplement for the main working of surface activity derived from both the hydrophobic and hydrophilic properties of the coating. The role of said agent (C) is only limited to the control of botanical aquatic organisms just coming in touch with the fishnet fiber or rope surface.

As already stated, if the amount of said agent is too excessive, there is a clear decrease in the time duration of the antifouling effect and a decrease in the antifouling effect itself. Thus, in this invention, the amount of said antifouling agent (C) is very important, and it must be, in total, 0.5 to 20% by weight, and preferably 1 to 12% by weight of the total weight of the phenol compound (A)+water-repellent compound (B)+said antifouling agent (C).

If the said amount is lower than the limit of 0.5% by weight, there is no particular additive effect.

Whereas, if the amount of the agent exceeds the upper limit of 20% by weight, there are undesirable effects as abovementioned.

In this respect, the inventors are of the opinion that since the agent (C) is liable to be easily hydrolyzed, if there are too large a quantity of these compounds (C) in the antifouling composition, there causes an unbalance in the desired surface activity of the coating due to an undesired increase in the hydrophilic nature of the coating through hydrolysis, for which reason the antifouling effect itself must be decreased.

When the limited quantity of said compound (C) is added to the composition of the specific phenol compound (A) and particular water-repellent compound (B), a very effective antifouling paint in both its synergistic effect and long-lasting effect can be obtained.

Furthermore, very surprisingly, botanical aquatic organisms are effectively controlled, which effect can never be expected with only the combination of the phenolic compound (A) and the water-repellent organic compound (B), and with the single use of said antifouling agent (C) in an antifouling paint.

The phenol compound (A) used as the first active ingredient of the present antifouling composition may be represented by the formula:

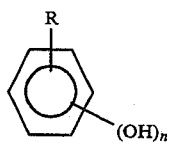
(I)

in which R is a linear or branched alkyl having 4 to 2 carbon atoms and n is an integer of 1–5, or by the formula:

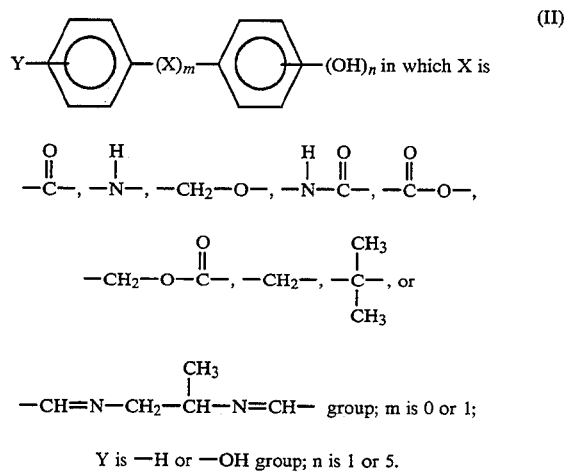

(II)

Y is —H or —OH group; n is 1 or 5.

Examples of the phenol compound (II) are 2,4-dihydroxybenzophenone

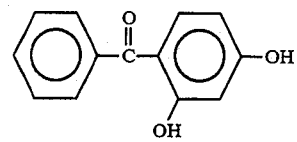

hydroxy benzophenone

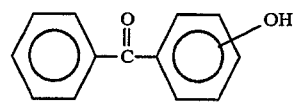

2,3,4,-trihydroxy benzophenone

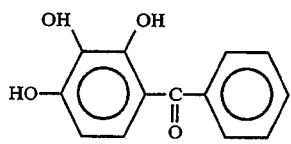

hydroxy diphenylimine

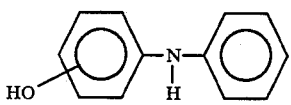

benzyloxyphenol

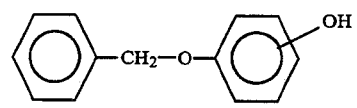

2-hydroxy-N-phenylbenzamide

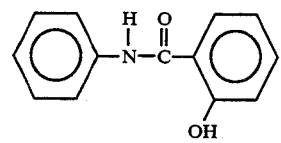

benzyl phenol

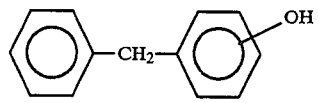

resorcin monobenzoic ester

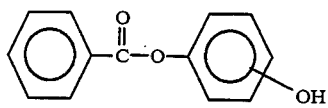

benzylsalicylate

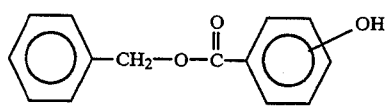

cumyl phenol

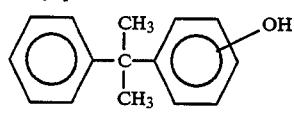

2,2-bis 4-hydroxy phenyl propane

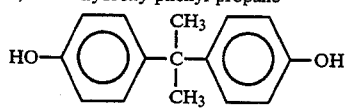

bis-4-hydroxy phenyl sulfone

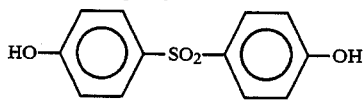

phenyl phenol

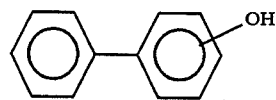

dihydroxy diphenyl

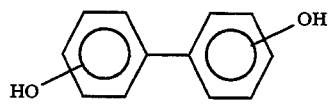

N,N′-disalicylidene 1,2-diaminopropane

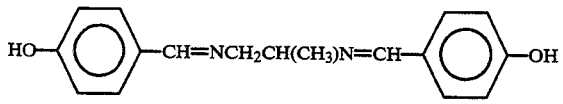

The water-repellent compounds used as the second active ingredient of the present composition are silicone-oil, petroleum wax and liquid paraffin.

One or two or more of these water repellent compounds are used as component (B).

In this invention, the term "silicone-oil" represents a polyorganosiloxane, which is an oil and has the following unit its structure:

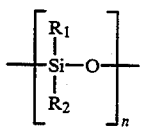

in which $R_1$ and $R_2$ each represents alkyl or phenyl group. Examples are polydimethyl siloxane, methyl phenyl polydisiloxane and the like, The petroleum wax as used herein denotes purified products crude oil whose properties are defined in JIS K2235. Examples are paraffin wax, microcrystalline wax, petrolatum and the like.

Highly purified petrolatum is vaseline defined in Japan Pharmacopoeia, which includes white vaseline, yellow vaseline and the like. The fluid paraffin as used herein denotes purified fractionates of crude oil, the properties of which are defined in JIS K2231, and various products are classified by viscosity and the like.

The invention shall be more fully explained by the following Examples and Comparative Examples.

EXAMPLES 1–7

The materials shown in Table 1 were placed in a high speed homodisper and well dispersed to obtain each antifouling paint.

Test fishnets (no knots, 60 ply thread 6 knots, 20×30 cm) were dipped in the antifouling paint obtained and thus treated nets were air-dried for 2 days.

Thereafter, thus treated fishnets were dipped in 1 meter depth, in sea-water at Tamano-bay area and antifouling effects were evaluated.

COMPARATIVE EXAMPLES 1–6

The materials shown in Table 2 the same procedures as stated in Examples 1–7 were repeated.

The test results are shown in Table 3.

TABLE 1

| Example | 1 | 2 | 3 | 4 | 5 | 6 | 7 |
|---|---|---|---|---|---|---|---|
| p-nonyl phenol | 25.0 | 25.0 | 25.0 | 15.0 | 35.9 | | |
| p-cumyl phenol | | | | 12.0 | | 25.0 | 35.9 |
| petrolatum | 14.5 | 14.5 | 14.5 | 8.9 | | 14.5 | |
| fluorodichloromethyl thiophthalimide | 0.4 | | | 2.0 | 2.0 | | 2.0 |
| dimethylphenyl-fluoro dichloromethyl thiosulfamide | | 0.4 | | 2.0 | | 0.2 | |
| dichlorophenyl dimethylurea | — | — | 0.4 | — | 2.0 | 0.4 | 2.0 |
| phthalocyanine blue | 0.1 | 0.1 | 0.1 | 0.1 | 0.1 | 0.1 | 0.1 |
| xylene | 60.0 | 60.0 | 60.0 | 60.0 | 60.0 | 60.0 | 60.0 |
| alkyd resin | | | | | | | |
| vinyl resin | | | | | | | |
| WW rosine | | | | | | | |
| tetramethyl thiuram disulfide | | | | | | | |
| dioctyl phthalate | | | | | | | |
| acetone | | | | | | | |
| Total | 100.0 | 100.0 | 100.0 | 100.0 | 100.0 | 100.0 | 100.0 |

TABLE 2

| Comparative Example | 1 | 2 | 3 | 4 | 5 | 6 |
|---|---|---|---|---|---|---|
| p-nonyl phenol | 25.0 | 31.9 | | | 20.0 | |
| p-cumyl phenol | | | | | | 20.0 |
| petrolatum | 14.9 | | | | 20.0 | 20.0 |
| fluorodichloromethyl thiophthalimide | 0.2 | 4.0 | 4.0 | 15.0 | | |
| dimethylphenylfluoro dichloromethyl thiosulfamide | | | | 10.0 | | |
| dichlorophenyl dimethylurea | — | 4.0 | — | — | | |
| phthalocyanine blue | 0.1 | 0.1 | | 0.3 | 0.1 | 0.1 |
| xylene | 59.8 | 60.0 | 69.0 | 24.2 | 59.9 | 59.9 |
| alkyd resin | | | 15.0 | | | |
| vinyl resin | | | | 7.0 | | |
| WW rosine | | | | 10.0 | | |
| tetramethyl thiuram disulfide | | | 12.0 | | | |
| dioctyl phthalate | | | | 1.5 | | |
| acetone | | | | 32.0 | | |

TABLE 2-continued

| Comparative Example | 1 | 2 | 3 | 4 | 5 | 6 |
|---|---|---|---|---|---|---|
| Total | 100.0 | 100.0 | 100.0 | 100.0 | 100.0 | 100.0 |

TABLE 3

| | Dipping Test results | | | | |
|---|---|---|---|---|---|
| | Dipping period (months) | | | | |
| | 1 | 3 | 6 | 9 | 12 |
| Example | | | | | |
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 5 |
| | | | | | (0) |
| 6 | 0 | 0 | 0 | 0 | 0 |
| 7 | 0 | 0 | 0 | 0 | 0 |
| Comp. Ex. | | | | | |
| 1 | 0 | 0 | 5 | 10 | 10 |
| | | | (5) | (5) | (7) |
| 2 | 0 | 5 | 10 | 10 | 10 |
| | | (0) | (3) | (5) | (5) |
| 3 | 5 | 20 | 40 | 80 | 80 |
| | (0) | (5) | (20) | (40) | (40) |
| 4 | 5 | 5 | 10 | 20 | 20 |
| | (0) | (0) | (5) | (10) | (10) |
| 5 | 0 | 0 | 0 | 5 | 10 |
| | | | | (5) | (7) |
| 6 | 0 | 0 | 0 | 5 | 10 |
| | | | | (5) | (7) |

Each figure represents net-clogging %
figure within parenthesis shows net-clogging % by botanical lives

What is claimed is:

1. An antifouling composition consisting essentially of (A) at least one phenol compound represented by the formula:

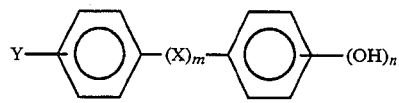

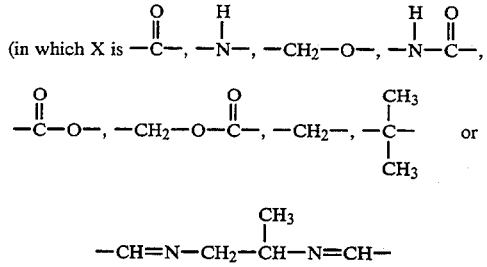

group; m is 0 or 1 ; Y is hydrogen atom or hydroxyl group; and n is an integer of 1 to 5) or the formula:

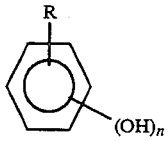

in which R is a linear or branched alkyl having 4 to 21 carbon atoms and n is an integer of 1–5.

(B) at least one water-repellent organic compound selected from group consisting of silicone oil, petroleum wax, and liquid paraffin, and (C) at least one antifouling agent selected from the group consisting of fluorodichloromethyl thiophthalimide, dimethyl phenyl fluorodichloromethyl thiosulfamide and dichlorophenyl dimethyl urea, the amount of said antifouling agent being 1–12% by weight of the total of said (A)+(B)+(C).

* * * * *